US012394504B2

(12) United States Patent
Uesawa

(10) Patent No.: US 12,394,504 B2
(45) Date of Patent: Aug. 19, 2025

(54) PREDICTING DEVICE, PREDICTING METHOD, PREDICTING PROGRAM, LEARNING MODEL INPUT DATA GENERATING DEVICE, AND LEARNING MODEL INPUT DATA GENERATING PROGRAM

(71) Applicant: MEIJI PHARMACEUTICAL UNIVERSITY, Tokyo (JP)

(72) Inventor: Yoshihiro Uesawa, Tokyo (JP)

(73) Assignee: MEIJI PHARMACEUTICAL UNIVERSITY, Tokyo (JP)

( * ) Notice: Subject to any disclaimer, the term of this patent is extended or adjusted under 35 U.S.C. 154(b) by 1310 days.

(21) Appl. No.: 16/698,129

(22) Filed: Nov. 27, 2019

(65) Prior Publication Data

US 2020/0098450 A1 Mar. 26, 2020

Related U.S. Application Data

(63) Continuation of application No. PCT/JP2018/024835, filed on Jun. 29, 2018.

(30) Foreign Application Priority Data

Jun. 30, 2017 (JP) ................ 2017-129823
Jun. 28, 2018 (JP) ................ 2018-122565

(51) Int. Cl.
*G16C 20/30* (2019.01)
*G16C 20/70* (2019.01)
*G16C 20/80* (2019.01)

(52) U.S. Cl.
CPC ............. *G16C 20/30* (2019.02); *G16C 20/70* (2019.02); *G16C 20/80* (2019.02)

(58) Field of Classification Search
CPC ......... G16C 20/30; G16C 20/70; G16C 20/80
See application file for complete search history.

(56) References Cited

U.S. PATENT DOCUMENTS

| | | | |
|---|---|---|---|
| 5,526,281 | A | 6/1996 | Chapman et al. |
| 7,702,467 | B2 | 4/2010 | Duffy |
| 7,751,988 | B2 | 7/2010 | Kita et al. |
| 2004/0009536 | A1 | 1/2004 | Grass et al. |
| 2004/0199334 | A1 | 10/2004 | Kovesdi et al. |
| 2011/0172981 | A1* | 7/2011 | Al-Hashimi ......... G01N 24/087 703/11 |

FOREIGN PATENT DOCUMENTS

JP 2005-250721 A 9/2005

OTHER PUBLICATIONS

Berry et al., Practical Considerations in Virtual Screening and Molecular Docking, 2015, Emerging Trends in Computational Biology, Bioinformatics, and Systems Biology, p. 487-502 (Year: 2015).*
Crisp et al., Pencil-and-Paper Neural Networks: An Undergraduate Laboratory Exercise in Computational Neuroscience, Jun. 2015, 14(1), p. A13-A22 (Year: 2015).*
Yuan et al., Feature extracting and image retrieval based on AlexNet, 2016, Proc. of SPIE, 10033, p. 1-6 (Year: 2016).*
Wallach et al., AtomNet: A Deep Convolution Neural Network Bioactivity Prediction in Structure-based Drug Discovery, 2015, arXiv, p. 1-11 (Year: 2015).*
Atomwise, How AtomNet Technology Improves Drug Design Using Convolution Neural Networks, Dec. 2015, Atomwise, p. 1-9 (Year: 2015).*
Atomwise, AtomNET Technology has the Power to Impact Early Drug Discovery, 2018, p. 1-7 (Year: 2018).*
NumbersAllTheWayDown (hereinafter NATWD) (How to Treat an image as a vector for machine learning, 2023, p. 1-14; newly cited (Year: 2023).*
Japanese Office Action for corresponding Japanese Application No. 2018-122565, dated Jul. 20, 2022, with English translation.
Hansen et al., "Benchmark Data Set for in Silico Prediction of Ames Mutagenicity"., J. Chem. Inf. Model., vol. 49, pp. 2077 to 2081, 2009.
International Preliminary Report Patentability and Written Opinion of the International Searching Authority (Forms PCT/IB/373, PCT/ISA/237), dated Dec. 31, 2019, for International Application No. PCT/JP2018/024835, with an English translation.
International Search Report (Form PCT/ISA/210), dated Aug. 28, 2018, for International Application No. PCT/JP2018/024835, with an English translation.
Kazius et al., "Derivation and Validation of Toxicophores for Mutagenicity Prediction"., J. Med. Chem, vol. 48, No. 1, pp. 312 to 320, 2005.
Ma et al., "Deep Neural Nets as a Method for Quantitative Structure-Activity Relationships"., Journal of Chemical Information and Modeling, vol. 55, pp. 263 to 274, Jan. 30, 2015.
Netzeva et al., "Current Status of Methods for Defining the Applicability Domain of (Quantitative) Structure-Activity Relationships"., The Report and Recommendations of ECVAM Workshop 52, pp. 1 to 19, 2005.
Tong et al., "Evaluation of Quantitative Structure-Activity Relationship Methods for Large-Scale Prediction of Chemicals Binding to the Estrogen Receptor"., Journal of Chemical Information and Computer Sciences, vol. 38, pp. 669 to 677, May 20, 1998.
Xu et al., "In silico Prediction of Chemical Ames Mutagenicity"., J. Chem. Inf. Model., vol. 52, No. 11, pp. 2840 to 2847, Oct. 2, 2012.
Chinese Office Action and Search Report for corresponding Chinese Application No. 201880044194.1, dated Mar. 30, 2023, with English translation.

(Continued)

*Primary Examiner* — Kaitlyn L Minchella
(74) *Attorney, Agent, or Firm* — Birch, Stewart, Kolasch & Birch, LLP

(57) ABSTRACT

An activity of a target compound is suitably predicted based on a structure of the target compound. A predicting device includes: a generating unit that captures a structural model of the target compound relatively from a plurality of directions with a virtual camera to generate a plurality of captured images; and a predicting unit that uses a learning model to predict the activity of the target compound from the plurality of captured images generated by the generating unit.

9 Claims, 7 Drawing Sheets

(56) References Cited

OTHER PUBLICATIONS

Barigye et al., "2D-Discrete Fourier Transform: Generalization of the MIA-QSAR strategy in molecular modeling," Chemometrics and Intelligent Laboratory Systems, vol. 143, 2015 (published online Mar. 4, 2015), pp. 79-84.
Extended European Search Report for corresponding European Application No. 18824219.2, dated Jun. 22, 2020.
Freitas et al., "MIA-QSAR: a simple 2D image-based approach for quantitative structure-activity relationship analysis," Journal of Molecular Structure, vol. 738, 2005, pp. 149-154.
Goh et al., "Chemception: A Deep Neural Network with Minimal Chemistry Knowledge Matches the Performance of Expert-developed QSAR/QSPR Models," arxiv.org, Cornell Univeristy Library, Jun. 21, 2017, pp. 1-38.
Wallach et al., "AtomNet: A Deep Convolutional Neural Network for Bioactivity Prediction in Structure-based Drug Discovery," retrieved from URL: https://arxiv.org/pdf/1510.02855.pdf, Oct. 10, 2015, pp. 1-11.
Indian Office Action for corresponding Indian Application No. 201947053360, dated Feb. 10, 2022, with an English translation.

\* cited by examiner

PREDICTING DEVICE, PREDICTING METHOD, PREDICTING PROGRAM, LEARNING MODEL INPUT DATA GENERATING DEVICE, AND LEARNING MODEL INPUT DATA GENERATING PROGRAM

CROSS-REFERENCE TO RELATED APPLICATIONS

The present application is a Continuation of PCT International Application No. PCT/JP2018/024835 filed on Jun. 29, 2018 claiming priorities under 35 U.S.C § 119(a) to Japanese Patent Application No. 2017-129823 filed on Jun. 30, 2017 and Japanese Patent Application No. 2018-122565 filed on Jun. 28, 2018. Each of the above applications is hereby expressly incorporated by reference, in its entirety, into the present application.

BACKGROUND OF THE INVENTION

1. Field of the Invention

One aspect of the present invention relates to a predicting device, a predicting method and a predicting program that use a learning model, and a learning model input data generating device and a learning model input data generating program.

2. Description of the Related Art

The difference in physiological activity for each chemical substance seems to derive from a chemical structure. A quantitative structure-activity relationship (QSAR) prediction model is to express a rule established between the chemical structure and the physiological activity as mathematical model, Even in a chemical substance having an unknown physiological activity, construction of the quantitative structure-activity relationship prediction model enables to predict activity of the substance without an experiment (see Patent Literatures 1 to 4).

In the conventional method of constructing a quantitative structure-activity relationship model, first, as indicated in Table 1 below, a chemical structure is converted into various numerical groups called chemical structure descriptors. Then, a mathematical model is constructed from the chemical structure descriptors by statistical analysis or machine learning. The chemical structure descriptors are usually calculated into hundreds to thousands of types using dedicated software. A combination of the chemical structure descriptors is directly related to high versatility of the quantitative structure-activity relationship prediction model, and is selected, for example, manually.

TABLE 1

| Compound | MW | ALOGP | TPSA (Tot) | nH | nC | nN | nO | G (N ... N) | G(0 ... 0) | ... |
|---|---|---|---|---|---|---|---|---|---|---|
| Compound 1 | 130.09 | −1.102 | 65.72 | 3 | 4 | 2 | 2 | 0 | 4.511 | ... |
| Compound 2 | 151.18 | 0.683 | 49.33 | 9 | 8 | 1 | 2 | 0 | 6.605 | ... |
| ... | ... | ... | ... | ... | ... | ... | ... | ... | ... | ... |

Further, there are known an international activity prediction competition (Tox21DataChallenge2014) for competing construction of a superior quantitative structure-activity relationship prediction model.

CITATION LIST

Patent Literature 1: U.S. Pat. No. 7,702,467
Patent Literature 2: U.S. Pat. No. 7,751,988
Patent Literature 3: U.S. Patent Application Publication No. 2004/0009536
Patent Literature 4: U.S. Patent Application Publication No. 2004/0199334

SUMMARY OF THE INVENTION

In the related art, as described above, it is necessary to carefully select a combination of chemical structure descriptors so as to improve prediction accuracy. It is very useful when the prediction accuracy can be improved without selecting a combination of chemical structure descriptors.

One aspect of the present invention has been made in consideration of the above problem, and aims to provide a novel technique for suitably predicting an activity of a target compound based on a structure of the target compound.

In order to solve the above problem, a predicting device according to an aspect of the present invention is a predicting device which predicts an activity of a target compound that based on a structure of the target compound, the predicting device including: a generating unit configured to capture images of a structural model of the target compound relatively from a plurality of directions with a virtual camera to generate a plurality of captured images; and a predicting unit configured to predict the activity of the target compound from the plurality of captured images generated by the generating unit, using a learning model.

Further, a predicting method according to another aspect of the present invention is a predicting method of predicting an activity of a target compound, based on a structure of the target compound, the predicting method including: a generating step, by a computer, of capturing images of a structural model of the target compound relatively from a plurality of directions with a virtual camera to generate a plurality of captured images; and a predicting step, by a computer, of predict the activity of the target compound from the plurality of captured images generated in the generating step, using a learning model.

In addition, a learning model input data generating device according to further another aspect of the present invention is a learning model input data generating device which generates input data of a learning model, wherein the learning model is a learning model configured to receive, as an input, a plurality of captured images obtained by capturing images of a structural model of a target compound with a virtual camera relatively from a plurality of directions, and output prediction information of an activity of the target compound, and the learning model input data generating device includes a generating unit configured to capture images of a structural model of the target compound relatively from a plurality of directions with a virtual camera to generate a plurality of captured images.

One aspect of the present invention, an activity of a target compound can be suitably predicted based on a structure of the target compound.

DESCRIPTION OF THE PREFERRED EMBODIMENTS

Embodiment 1

Figure 1:
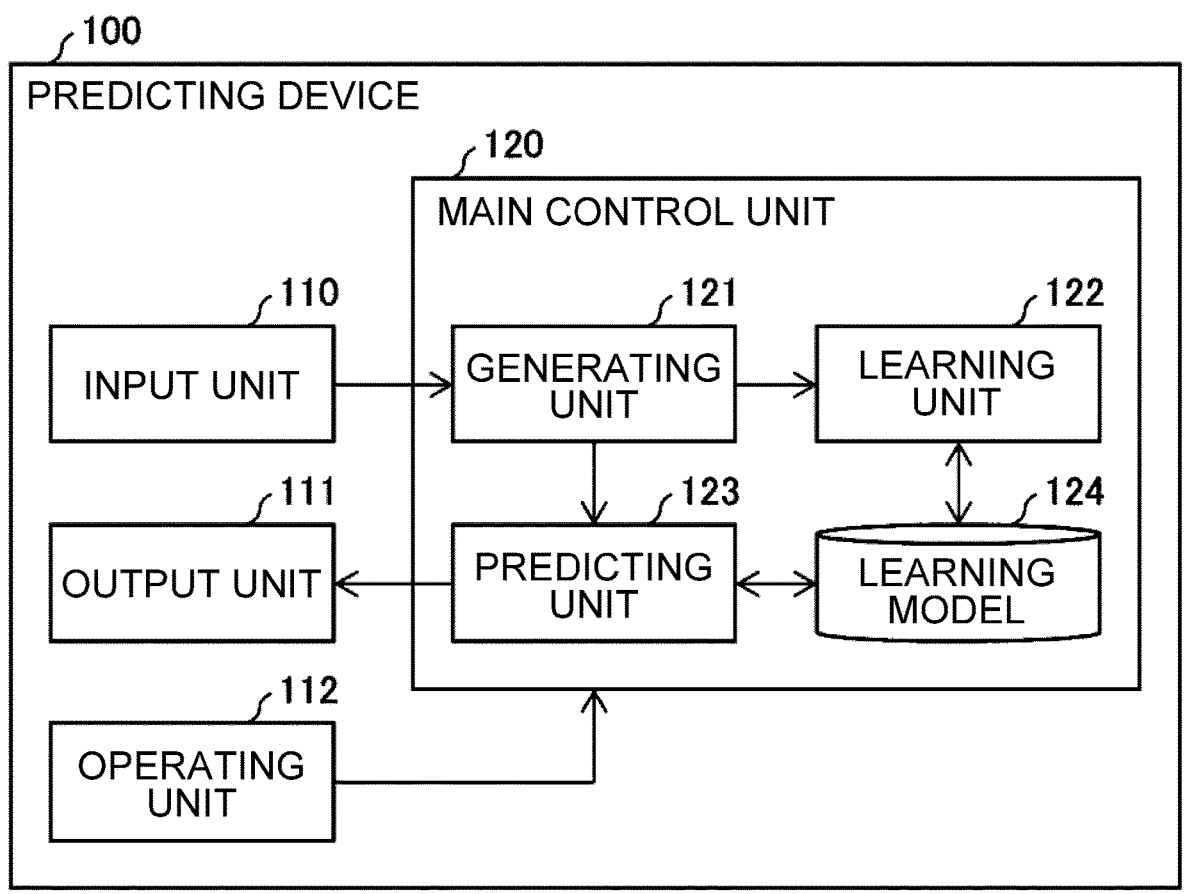
FIG. 1 is a functional block diagram illustrating an example of a schematic configuration of a predicting device according to an embodiment of the present invention.

An embodiment of the present invention will be described in detail below. FIG. 1 is a functional block diagram illustrating an example of a schematic configuration of a predicting device 100 according to the embodiment of the present invention. The predicting device 100 includes an input unit 110, an output unit 111, an operating unit 112, and a main control unit 120. The main control unit 120 includes a generating unit 121, a learning unit 122, a predicting unit 123, and a learning model 124.

The predicting device 100 is a predicting device that predicts activity of a target compound based on a structure of the target compound. In one aspect, the predicting device 100 predicts activity of the target compound using the learning model 124 based on data indicating the structure of the target compound input from the input unit 110 and outputs the result using the output unit 111. Moreover, in one aspect, the predicting device 100 performs learning of the learning model 124 based on data indicating a structure of a reference compound input from the input unit 110 and data indicating activity of the reference compound. In the description, note that the reference compound is a compound serving as a source of information in the learning of the learning model 124 and the target compound is a compound whose activity is predicted by the learning model 124.

In one aspect, the predicting device 100 also functions as a learning model input data generating device that generates input data to be input to the learning model 124. Furthermore, in a modified example, the predicting device may be configured by: a learning model input data generating device including an input unit 110 and a generating unit 121; and a learning model device including a learning unit 122, a predicting unit 123 and a learning model 124.

(Input Unit)

The input unit 110 receives data indicating the structure of the target compound or data indicating the structure of the reference compound, and data indicating the activity of the reference compound which are input to the predicting device 100. The input unit 110 reads a data file stored in a storage medium or receives data from another device via a wired or wireless network, thereby receiving the input data described above.

(Data indicating Structure of Compound)

The compound used as the target compound and the reference compound are not particularly limited in terms of a structure, an origin, and physical properties, and may be a natural compound, a synthetic compound, a high molecular compound, a low molecular compound and so on, for example. Data indicating the structure of the compound may be obtained from a public database such as PubChem (pubchem.ncbi.nlm.nih.gov), or may be newly created. A format of the data indicating the structure of the compound is not particularly limited, and may be a known data format such as an SDF format, for example.

The data indicating the structure of the compound can be created using, for example, a known software (for example, Corina (mn-am.com/products/corina) or the like) that generates a three-dimensional structure from a two-dimensional chemical structure. Various conditions (for example, whether to be in a vacuum or in an aqueous solution, temperature conditions, and pH) at the time of generation of the three-dimensional structure are not particularly limited, and, for example, data indicating a three-dimensional structure satisfying specific conditions (for example, most stable in a vacuum) may be created. In addition, data indicating the three-dimensional structure may be created by estimating a three-dimensional structure in which a desired protein is bound by a known docking algorithm (for example, DOCK). Thus, more advanced prediction can be performed.

In one aspect, a plurality of data indicating a three-dimensional structure may be generated for one compound. For example, in consideration of the degree of freedom of bond between atoms in an aqueous solution, various three-dimensional structures may be generated by rotating a rotatable functional group in a molecule for each molecule. In addition, various three-dimensional structures may be generated in consideration of molecular vibration due to thermal energy by a molecular dynamics (MD) simulation. Thus, much more images can be generated by the generating unit 121 to be described below, and prediction can be performed with higher accuracy.

(Data indicating Activity of Compound)

Data indicating the activity of the reference compound may be obtained from, for example, a public database such as PubChem (pubchem.ncbi.nlm.nih.gov), or may be obtained experimentally. A format of the data indicating the activity of the reference compound is not particularly limited. The data format may be data indicating a binary value for determining whether to have a desired activity, data indicating a value selected from a plurality of category values, or data indicating continuous variables.

The desired activity is not particularly limited, and may be various activities of a pharmaceutical activity, a physiological activity, a biochemical activity, and toxicity, for example.

(Output Unit)

The output unit 111 is to output the prediction result of the activity of the target compound by the predicting unit 123. For example, in one aspect, the output unit 111 may output the prediction result to a display device in a form of image data or character data, or the output unit 111 may output a data file including image data, character data, or binary data indicating the prediction result, or the output unit 111 may transmit image data, character data, or binary data indicating the prediction result to another device via a wired or wireless network.

(Operating Unit)

The operating unit 112 receives a user's operation to the predicting device 100. The operating unit 112 may be, for example, a keyboard, a mouse, a trackball, a touch pad (including a touch panel), an optical sensor, and a microphone for voice input.

(Main Control Unit)

The main control unit 120 includes one or more computers. When the main control unit 120 includes a plurality of computers, the plurality of computers may be connected to each other in a wired or wireless manner and may share functions of the main control unit 120.

(Learning Model)

The learning model 124 is a learning model that performs machine learning. Preferably, the learning model 124 is a learning model that receives, as an input, a plurality of captured images obtained by capturing a structural model of the target compound from a plurality of directions with a virtual camera and outputs prediction information on the activity of the target compound. More preferably, the learning model 124 uses a learning model that performs deep learning (Deep Learning) and can use, for example, a convolutional neural network such as AlexNet, CaffeNet, GoogLeNet, or VGG net.

The prediction information on the activity of the target compound is not particularly limited, and may be information indicating the probability that the target compound has a desired activity, information indicating the prediction result of whether the target compound has a desired activity, or a score corresponding to the possibility that the target compound has a desired activity, for example.

In one aspect, the learning model 124 may be a combination of a plurality of learning models. That is, the learning model 124 may be a combination of: a first learning model that receives, as an input, a plurality of captured images obtained by capturing a structural model of the target compound in a plurality of directions with a virtual camera and outputs a feature vector; and a second learning model that receives a feature vector as an input and outputs the prediction information on the activity of the target compound. In this case, the first learning model may be a learning model that receives, as an input, a plurality of captured images obtained by capturing a structural model of the target compound in a plurality of directions, but may preferably use a learning model that performs deep learning. In addition, the second learning model may use a learning model that performs deep learning, or may use a learning model that does not perform deep learning.

(Generating Unit)

Figure 2:
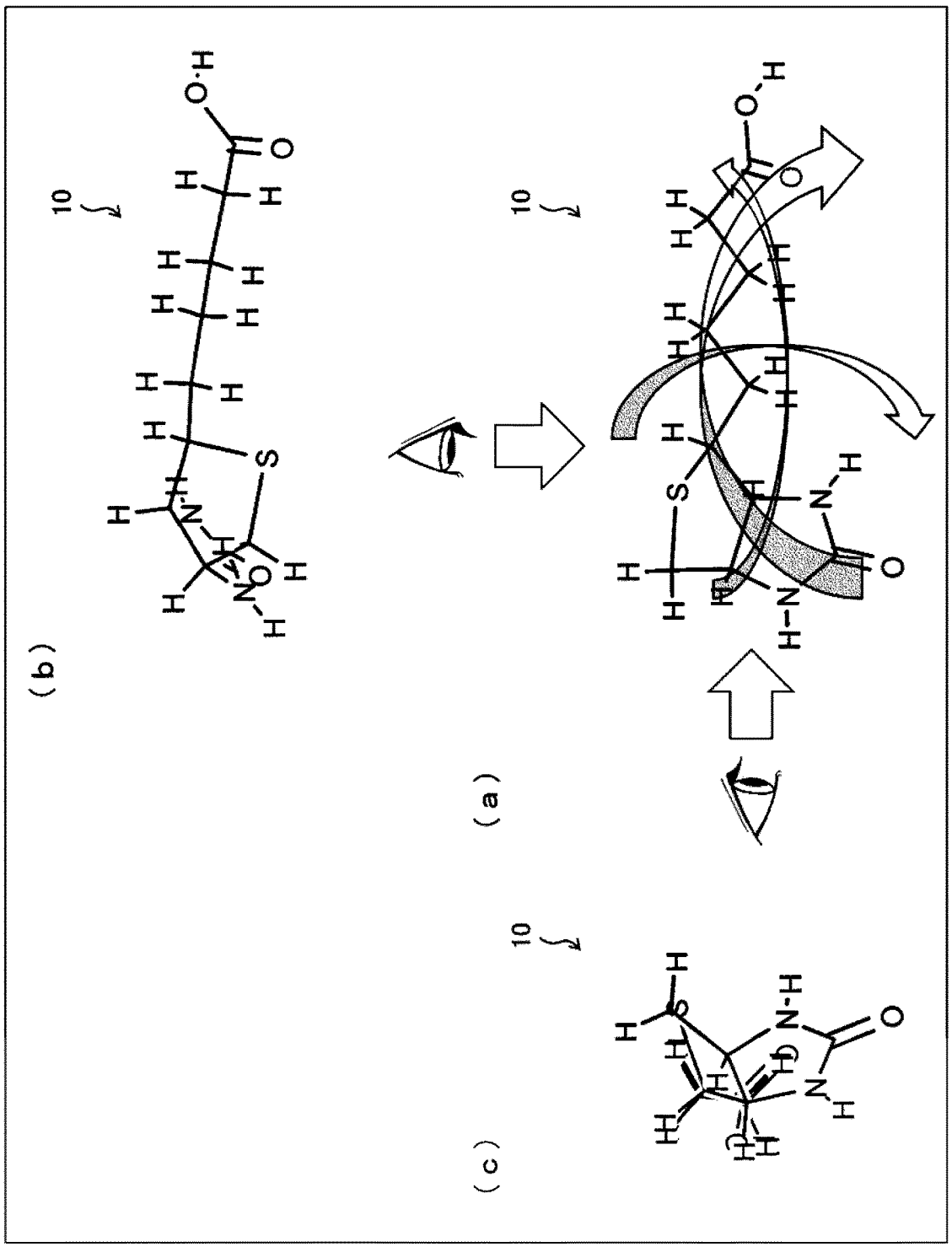
FIG. 2 is a schematic diagram schematically illustrating an example of an image generation in the embodiment of the present invention.

The generating unit 121 captures images of a structural model of the target compound or the reference compound relatively from a plurality of directions with a virtual camera to generate a plurality of captured images (snapshots). FIG. 2 is a schematic diagram illustrating schematically an example of image generation in the present embodiment. As illustrated in FIG. 2, the generating unit 121 rotates a structural model 10 of the target compound disposed in a virtual space, and captures images of the structural model relatively from a plurality of directions with a virtual camera, thereby generating captured images (images illustrated in (a) to (c) portions of FIG. 2). Here, the generating unit 121 may capture images of the structural model 10 relatively from a plurality of directions by moving the virtual camera instead of rotating the structural model 10. Note that the "captured image" in the description is also referred to as a snapshot, means an image obtained by capturing images of the structural model disposed in the virtual space with the virtual camera, and also includes an image calculated directly from coordinate data without construction of the structural model when having the same contents as the image.

Generation of the structural model and capturing of its images with the virtual camera can be performed using known software (for example, Jmol (jmol.sourceforge.net/), VMD (www.ks.uiuc.edu/Research/vmd/), UCSF Chimera (www.cgl.ucsf.edu/chimera/), Rasmol (www.umass.edu/microbio/rasmol/), PyMOL (www.pymol.org/), or the like) that enables a three-dimensional display of a molecular structure and capturing its images with the virtual camera.

In one aspect, an image file of the captured image to be generated may be, for example, input as a set of RGB three-color dots, and may include position information in a two-dimensional plane and three types of color information that are digitized. The size of the captured image generated by the generating unit 121 is not particularly limited, and may be appropriately adjusted according to the size of the target compound and the reference compound. For example, the size of the captured image may be 128 pixels×128 pixels, 256 pixels×256 pixels, 512 pixels×512 pixels, or 1024 pixels×1024 pixels. In addition, a color depth is not particularly limited, and may be, for example, in the range of 1 to 64 bpp, and preferably in the range of 8 to 32 bpp.

Figure 3:
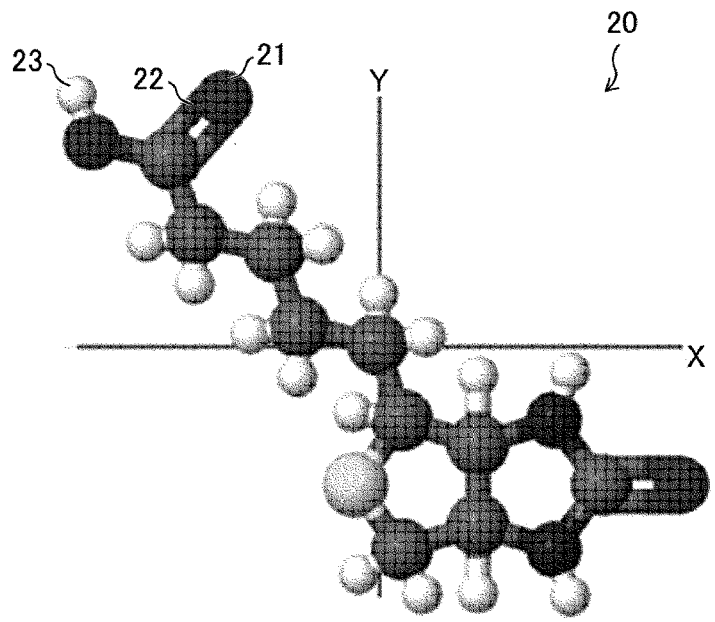
FIG. 3 is a schematic diagram illustrating an example of the image generation in the embodiment of the present invention in detail.
Figure 3:
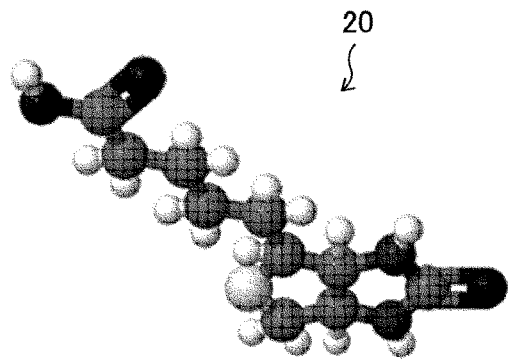
Figure 3:
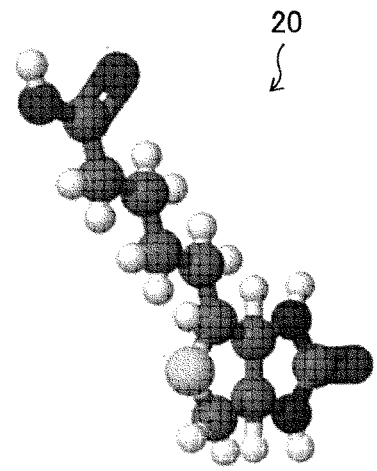
Figure 3:
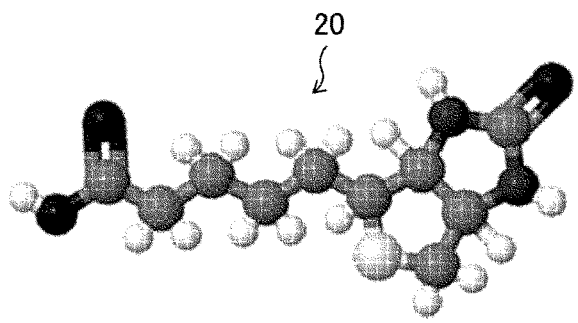

FIG. 3 is a schematic diagram illustrating in detail an example of image generation in the present embodiment. In FIG. 3, a structural model 20 is displayed with a Ball-and-Stick display. Note that the Ball-and-Stick display is a display mode in which atoms are indicated by balls and bonds are indicated by sticks. However, the present embodiment is not limited thereto, and the structural model may be displayed with, for example, a Wireframe display that shows structural model only by bonds, a Spacefill display that fills a space with atoms, a Surface display that displays a surface of molecules in contact with an aqueous solution, and a Ribbons display that schematically shows a structure of protein.

As illustrated in (a) portion of FIG. 3, the structural model 20 includes atoms 21, bonds 22, and hydrogen atoms 23. Note that the atom 21 represents an atom other than the hydrogen atom. In one aspect, the hydrogen atom 23 may not be included in the structural model 20. In the structural model 20, colors of the atoms 21 vary depending on types of the atoms, but are not limited thereto. The colors of the atoms 21 may be the same as each other. Or, the types of atoms are appropriately grouped, and the colors of the atoms 21 may differ depending on the group to which the atoms belong.

Further, a radius of the atom 21 is not particularly limited; for example, an upper limit of the radius can be 50% or less, 40% or less, 30% or less, 20% or less, 10% or less, 5% or less, 3% or less, or 1% or less of the Van der Waals radius; and a lower limit of the radius can be 0.1% or more, 0.3% or more, 0.7% or more, or 1% or more of the Van der Waals radius. However, the radius of the atom is preferably 0.1% or more and 30% or less, more preferably 0.1% or more and 10% or less, and particularly preferably 0.1% or more and 3% or less.

In addition, a thickness of the bond 22 is not particularly limited: for example, an upper limit of the thickness can be 300 milli-angstroms or less, 200 milli-angstroms or less, 100 milli-angstroms or less, 50 milli-angstroms or less, 30 milli-angstroms or less, or 20 milli-angstroms or less; and a lower limit of the thickness can be 1 milli-angstrom or more, 2 milli-angstroms or more, 5 milli-angstroms or more, or 10 milli-angstroms or more. However, the thickness of the bond is preferably 1 milli-angstrom or more and 200 milli-angstroms or less, more preferably 2 milli-angstroms or more and 100 milli-angstroms or less, and particularly preferably 2 milli-angstroms or more and 30 milli-angstroms or less.

In one aspect, the generating unit 121 captures images of the structural model 20 while rotating the virtual camera around at least one axis relatively to the structural model 20. The axis is not particularly limited, but can be, for example, one or more axes selected from an X-axis, a Y-axis, and a Z-axis of the virtual space where the structural model 20 is disposed. For example, (b) portion of FIG. 3 illustrates a captured image obtained in a state where the structural model 20 is rotated by 45 degrees around the X-axis illustrated in (a) portion of FIG. 3. Further, (c) portion of FIG. 3 illustrates a captured image obtained in a manner that the structural model 20 is captured in a state of being rotated by 45 degrees around the Y-axis illustrated in (a) portion of FIG. 3, and (d) portion of FIG. 3 illustrates a captured image obtained in a state where the structural model 20 is rotated by 45 degrees around the Z-axis orthogonal to the X-axis and the Y-axis illustrated in (a) portion of FIG. 3.

Here, the rotation angle is not particularly limited: the capturing may be performed at every angle (at an angle interval) arbitrary selected from a range of 1 degree to 180 degrees, preferably at every angle arbitrary selected from a range of 1 degree to 90 degrees, and more preferably at every angle arbitrary selected from a range of 1 degree to 45 degrees. Further, the rotation angle may be changed for every capturing. For example, the capturing can be performed at every 30 degrees, at every 45 degrees, or at every 90 degrees. When the structural model 20 is rotated around a plurality of axes, capturing is performed so as to cover a possible angle range for each axis. That is, when the capturing is performed every 90 degrees around the X-axis and the Y-axis, the number of images to be captured per compound is 16 (4×4=16). Further, when the capturing is performed every 45 degrees around the X-axis, the Y-axis, and the Z-axis, the number of images to be captured per compound is 512 (8×8×8=512). In this way, when the capturing is performed to cover the possible angle range, it is possible to take snapshots of the structural model 20 viewed from all directions.

(Learning Unit)

Using a known method, the learning unit 122 causes the learning model 124 to learn correspondence between each captured image of the reference compound generated by the generating unit 121 and the activity of the reference compound. In one aspect, using a known deep learning algorithm, the learning unit 122 causes the learning model 124 to learn correspondence between each captured image of the reference compound generated by the generating unit 121 and the activity of the reference compound. The learning unit 122 may use, for example, a known deep learning framework such as Digits (NVIDIA Corp.).

(Predicting Unit)

Using the learning model 124 that learns the correspondence between each captured image of the target compound generated by the generating unit 121 and the activity of the target compound, the predicting unit 123 predicts the activity of the target compound from each captured image of the target compound generated by the generating unit 121. The predicting unit 123 may use, for example, a known deep learning framework such as Digits (NVIDIA Corp.).

In one aspect, if the learning model 124 outputs a value indicating the probability that the target compound has a desired activity when each captured image of the target compound is input, the predicting unit 123 can predict whether the target compound has the desired activity by acquiring a representative value (for example, a median value, an average value, or a total value) of each output value of the learning model 124 when each captured image of the target compound is input and comparing the representative value with a threshold value.

Although any value can be used as the threshold value, it is preferable to use a threshold value calculated by performing ROC analysis of an output value when each captured image of the reference compound is input to the learning model 124 which has already learned.

(Learning Processing)

Figure 4:
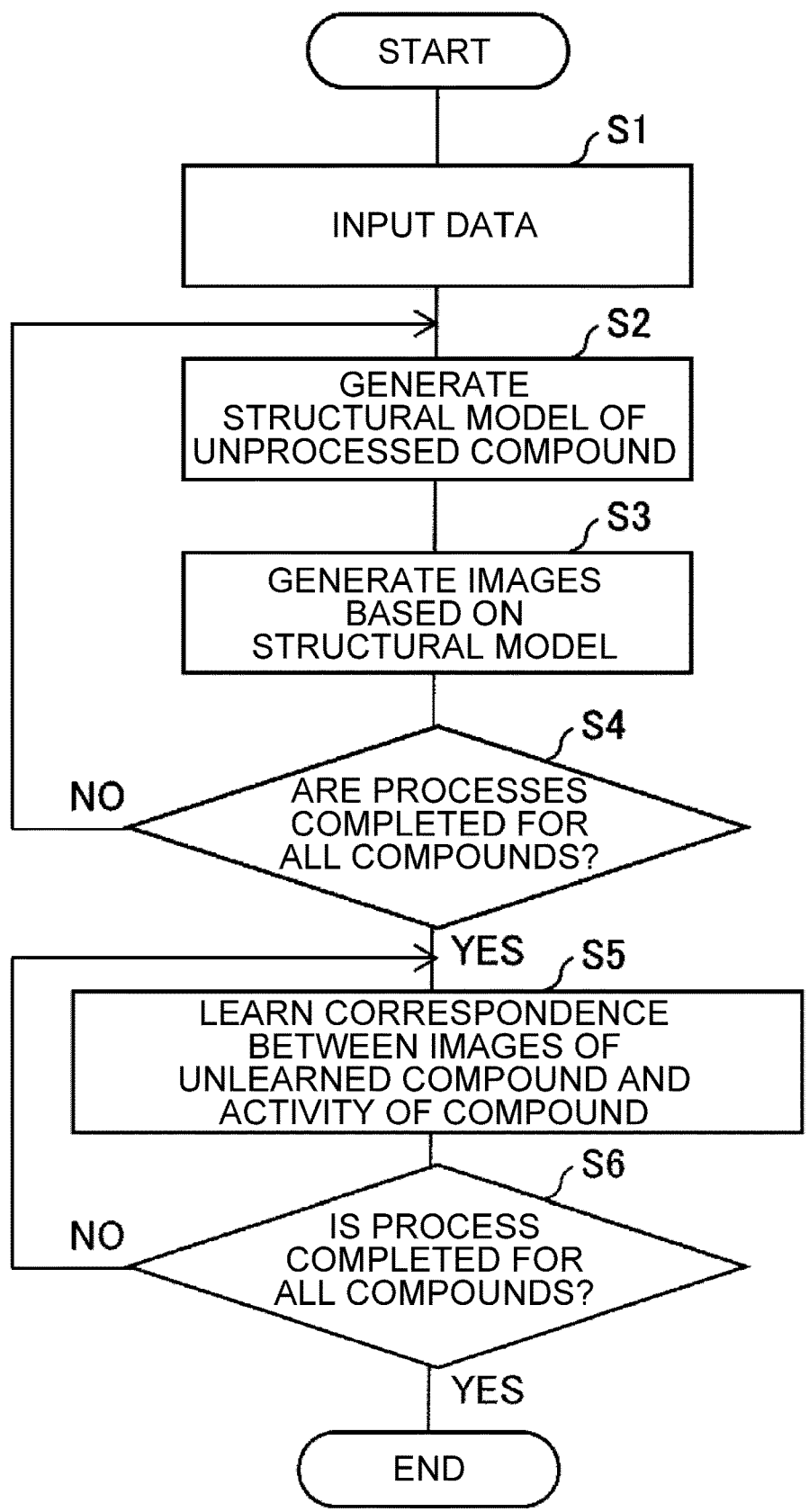
FIG. 4 is a flowchart illustrating an example of a flow of learning processing in the embodiment of the present invention.

FIG. 4 is a flowchart illustrating an example of a flow of learning processing in the embodiment of the present invention. First, when learning processing is started by an operation through the operating unit 112, the generating unit 121 acquires data indicating a structure of a reference compound and data indicating an activity of the reference compound, via the input unit 110 (step S1). Subsequently, the generating unit 121 generates, based on data indicating a structure of an unprocessed reference compound out of the data that are input in step S1, a structural model of the unprocessed reference compound (step S2). Subsequently, the generating unit 121 captures images of the structural model of the reference compound which is generated in step S2, relatively from a plurality of directions with the virtual camera to generate a plurality of captured images (step S3). In one aspect, the generating unit 121 captures images of the structural model in step S3 while rotating the virtual camera relatively to the structural model which is generated in step S2, around at least one axis to generate a plurality of captured images. When the above-described processes are completed for all the reference compounds included in the data input in step S1 (yes in step S4), the process proceeds to step S5. When the above-described processes are not completed (no in step S4), the process returns to step S2.

Next, the learning unit 122 causes, using a known machine learning algorithm (particularly, a deep learning algorithm), the learning model 124 to learn correspondence between each captured image of the reference compound generated in step S3 and the activity of the reference compound input in step S1 (step S5). Furthermore, when the learning unit 122 uses Digits, the captured images are stored in folders different for each teaching data (for example, with a desired activity=1, without a desired activity=0) assigned to the reference compound in advance, and thus step S5 can be suitably executed. In addition, teaching data of the reference compound corresponding to each captured image may be linked. When step S5 is completed for all the reference compounds included in the data input in step S1 (yes in step S6), the learning processing is ended. When step S5 is not completed for all the reference compounds (no in step S6), the process returns to step S5.

As described above, the predicting device 100 sets the learning model 124 as an already-learned model (learned model) that receives, as an input, a plurality of captured images obtained by capturing images of a structural model of a compound from a plurality of directions with a virtual camera and outputs prediction information on an activity of the compound.

(Predicting Processing)

Figure 5:
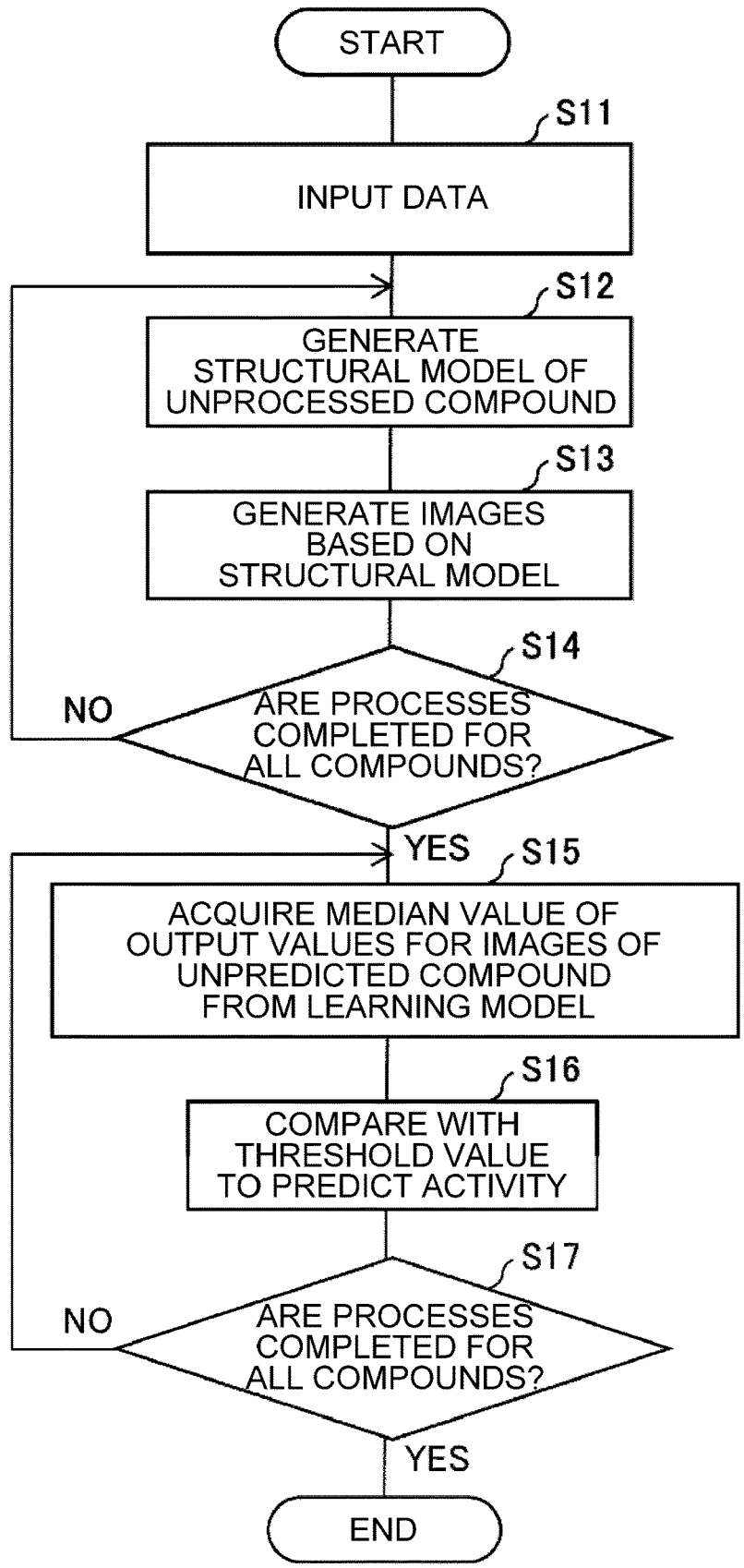
FIG. 5 is a flowchart illustrating an example of a flow of predicting processing in the embodiment of the present invention.

FIG. 5 is a flowchart illustrating an example of a flow of predicting processing in the embodiment of the present invention. First, when predicting processing is started by an operation through the operating unit 112, the generating unit 121 acquires data indicating a structure of a target compound via the input unit 110 (step S11). Subsequently, the generating unit 121 generates, based on data indicating a structure of an unprocessed target compound out of the data that are input in step S11, a structural model of the unprocessed target compound (step S12). Subsequently, the generating unit 121 captures images of the structural model of the target compound which is generated in step S12 (step S13), with the virtual camera relatively from a plurality of directions to generate a plurality of captured images. In one aspect, in step S13, the generating unit 121 captures images of the structural model while rotating the virtual camera around at least one axis relatively to the structural model which is generated in step S12, to generate a plurality of captured images. When the above-described processes are completed for all the target compounds included in the data input in step S11 (yes in step S14), the process proceeds to step S15. When the above-described processes are not completed (no in step S14), the process returns to step S12.

Next, the predicting unit 123 inputs each captured image of the target compound generated in step S13 to the learning model 124 and acquires an output from the learning model 124. In one embodiment, when the output from the learning model 124 is a value indicating the probability that the target compound has a desired activity, the predicting unit 123 acquires a median value of the values output from the learning model 124 when respective captured images of one target compound are input (step S15). Then, the predicting unit 123 compares the median value acquired in step S15 with a threshold value and predicts whether the target compound has a desired activity (step S16). When steps S15 to S16 are completed for all the target compounds included in the data input in step S11 (yes in step S17), the predicting processing is ended. When steps S15 to 16 are completed for all the target compounds (no in step S17), the process returns to step S15.

As described above, the predicting device 100 can predict whether the target compound has a desired activity.

Effects of Present Embodiment

According to the present embodiment, it is possible to predict activities such as a drug effect, a toxicity, and an enzyme inhibitory activity for many compounds without experiment.

In particular, according to the present embodiment, enantiomers (mirror image isomers) can be identified because the input to the learning model 124 is images. In the conventional method which uses a descriptor, since descriptors take the same value between enantiomers, it is difficult to express an activity difference between the enantiomers when various compounds are used. On the other hand, according to the present embodiment, since the captured images include information for identifying the enantiomers, the information is also used for pattern recognition by the learning model 124, and the enantiomers can be identified. The present embodiment is very useful because cases when physiological activities are different between the enantiomers are universally seen.

In addition, the present embodiment is applicable to biased data when the learning model that performs deep learning is used in the learning model 124. That is, even when a ratio of the presence to absence of a desired activity for an input reference compound is an extreme ratio such as 1 to 10, good accuracy can be obtained. On the other hand, in the conventional method, the most accurate model can be constructed when a ratio of presence to absence of the activity in data is about 1:1, but it is difficult to handle biased data. As for toxicity and the like, only a part of compounds shows an activity, so the present embodiment is very useful.

Further, according to the present embodiment, since the captured images obtained by capturing images of the structural model in a plurality of directions are input to the learning model 124, data including information that comprehensively indicates the structure of the target compound can be input to the learning model, and thus it is possible to suitably predict the activity of the target compound. In particular, since the captured images obtained by capturing the structural model while relatively rotating the virtual camera around one or more axes are input to the learning model 124, data including information that more comprehensively indicates the structure of the target compound can be input to the learning model, and thus it is possible to more suitably predict the activity of the target compound.

In addition, since the size of atoms and bonds in the structural model is defined as described above, the inner atoms or bonds can be prevented from being hidden by the outer atoms or bonds, and information on the inner atoms or bonds can be included in the captured image. Thus, it is possible to suitably predict the activity.

In addition, since the colors of atoms in the structural model vary depending on the types of atoms, information on the types of atoms can be included in the captured image. Thus, it is possible to suitably predict the activity.

MODIFIED EXAMPLE

In the embodiment described above, the predicting unit 123 predicts, using the learning model 124, whether the target compound of a captured image has a desired activity for each of the captured images and then integrates the prediction results to predict the activity of the target compound, but the present invention is not limited thereto. For example, the predicting device can be configured so that the learning unit 122 causes the learning model 124 to learn correspondence between data obtained by integrating respective captured images of a reference compound and an activity of the reference compound, and the predicting unit 123 inputs data obtained by integrating respective captured images of a target compound to the learning model 124 to predict an activity of the target compound.

Further, in the embodiment described above, the predicting unit 123 compares the representative value of the respective output values of the learning model 124 with the threshold value to predict the activity of the target compound, but the present invention is not limited thereto. For example, the prediction device may be configured so that the learning unit 122 causes another learning model to learn correspondence between an output value of the learning model 124 at the time of the input of each captured image of a reference compound and an activity of the reference compound, and the predicting unit 123 inputs the respective output values of the learning model 124 to the other learning model to predict an activity of the target compound.

As described above, one aspect of the present invention has a feature in that the plurality of captured images obtained by capturing images of the structural model of the target compound with the virtual camera relatively from the plurality of directions is input to the learning model and the activity of the target compound is predicted based on the output from the learning model. Configurations other than that can take various aspects.

<Implementation Example with Software>

A control block of the predicting device 100 (the main control unit 120, in particular, the generating unit 121, the learning unit 122, and the predicting unit 123) can be implemented with a logic circuit (hardware) formed in an integrated circuit (IC chip) or the like or can be implemented by software.

In the latter case, the predicting device 100 includes a computer that executes instructions of a program that is software realizing each function. The computer includes, for example, at least one processor (control device) and at least one computer-readable recording medium in which the program is stored. An object of the present invention can be achieved in such a manner that the processor of the computer reads and executes the program from the recording medium. As the processor, for example, a CPU (Central Processing Unit) can be used. As an example of the recording medium, "a non-transitory tangible medium" such as a ROM (Read Only Memory), a tape, a disk, a card, a semiconductor memory, or a programmable logic circuit can be used. The recording medium may further include a RAM (Random Access Memory) for expanding the program. The program may be supplied to the computer via any transmission medium (such as a communication network or a broadcast wave) which can transmit the program. Note that one aspect of the present invention can also be implemented in a form of a data signal in which the program is embodied by electronic transmission and which is embedded in a carrier wave.

SUMMARY

A predicting device (100) according to aspect 1 of the present invention is a predicting device which predicts an activity of a target compound based on a structure of the target compound, the predicting device including: a generating unit (121) configured to capture images of a structural model (10, 20) of the target compound relatively from a plurality of directions with a virtual camera to generate a plurality of captured images; and a predicting unit (123) configured to predict the activity of the target compound from the plurality of captured images generated by the generating unit, using a learning model (124). According to the configuration described above, the activity of the target compound can be suitably predicted based on the structure of the target compound, without selection of a combination of descriptors. In addition, because the input to the learning model is images, enantiomers can be identified.

In the predicting device according to aspect 2 of the present invention defined in aspect 1, the predicting unit may use a learning model that performs at least machine learning and receives the plurality of captured images as an input. According to the configuration described above, the activity of the target compound can be suitably predicted.

In the predicting device according to aspect 3 of the present invention defined in aspect 1 or 2, the generating unit may capture the images of the structural model while rotating the virtual camera relatively to the structural model around at least one axis. According to the configuration described above, since it is possible to generate the captured images which cover comprehensively the structure of the target compound, the activity can be suitably predicted.

In the predicting device according to aspect 4 of the present invention defined in aspects 1 to 3, in the structural model, a color of an atom (21) of the target compound may vary depending on a type of the atom. According to the configuration described above, since it is possible to generate the captured images including information indicating a type of atom of the target compound, the activity can be suitably predicted.

A predicting method according to aspect 5 of the present invention is a predicting method of predicting an activity of a target compound based on a structure of the target compound, the predicting method including: a generating step, by a computer, of capturing images of a structural model of the target compound relatively from a plurality of directions with a virtual camera to generate a plurality of captured images: and a predicting step, by a computer, of predicting the activity of the target compound from the plurality of captured images generated in the generating step, using a learning model. According to the configuration described above, an effect equivalent to that of aspect 1 is achieved.

The predicting device according to each aspect of the present invention may be implemented by a computer. In this case, the scope of the present invention also includes a predicting program for the predicting device which causes a computer to operate as each unit (software element) included in the predicting device so that the computer implements the predicting device, and a computer-readable recording medium which stores the predicting program.

A learning model input data generating device (100) according to aspect 7 of the present invention is a learning model input data generating device which generates input data of a learning model, wherein the learning model is a learning model (124) configured to receive, as an input, a plurality of captured images obtained by capturing images of a structural model of a target compound with a virtual camera relatively from a plurality of directions, and output prediction information of an activity of the target compound, and the learning model input data generating device includes a generating unit (121) configured to capture images of a structural model of the target compound relatively from a plurality of directions with a virtual camera to generate a plurality of captured images. According to the configuration described above, an effect equivalent to that of aspect 1 is achieved.

The learning model input data generating device according to each aspect of the present invention may be implemented by a computer. In this case, the scope of the present invention also includes a learning model input data generating program for the learning model input data generating device which causes a computer to operate as each unit (software element) included in the learning model input data generating device so that the computer implements the learning model input data generating device, and a computer-readable recording medium which stores the learning model input data generating program.

The present invention is not limited to the embodiments described above, and various modifications can be made within the scope of the claims. An embodiment derived from a proper combination of technical means each disclosed in different embodiments is also included in the technical scope of the present invention. Further, a new technical feature can be formed by a combination of the technical means disclosed in the respective embodiments.

Example 1

One aspect of the present invention was performed using learning data based on 7320 types of compounds published on a website of Tox21DataChallenge2014 (tripod.nih.gov/ tox21/challenge/data.jsp) and test data based on 543 types of compounds that do not overlap with compounds of the learning data. A desired activity to be predicted was a mitochondrial membrane potential disturbing activity.

First, using Jmol (jmol.sourceforge.net/), structural models of the compounds were generated based on SDF files and a program (learning model input data generating program) was created for capturing and generating 512 captured images (snapshot, size: 512×512, 24 bpp) of the respective structural models with rotating the structural models around each of an X-axis, a Y-axis, and a Z-axis in 45-degree increments. The program was executed, the SDF files of learning data were input, and captured images of each compound were generated. The captured images of each compound were stored in predetermined folders depending on whether each compound had a mitochondrial membrane potential disturbing activity, and an unmodified AlexNet (University of Toronto) was allowed to learn using Digits (NVIDIA Corp.). In the learning, Digits was set to have a learning rate=0.001 and an epoch=1. The "epoch" indicates the number of times one learning data is allowed to be repeatedly learned.

Figure 6:
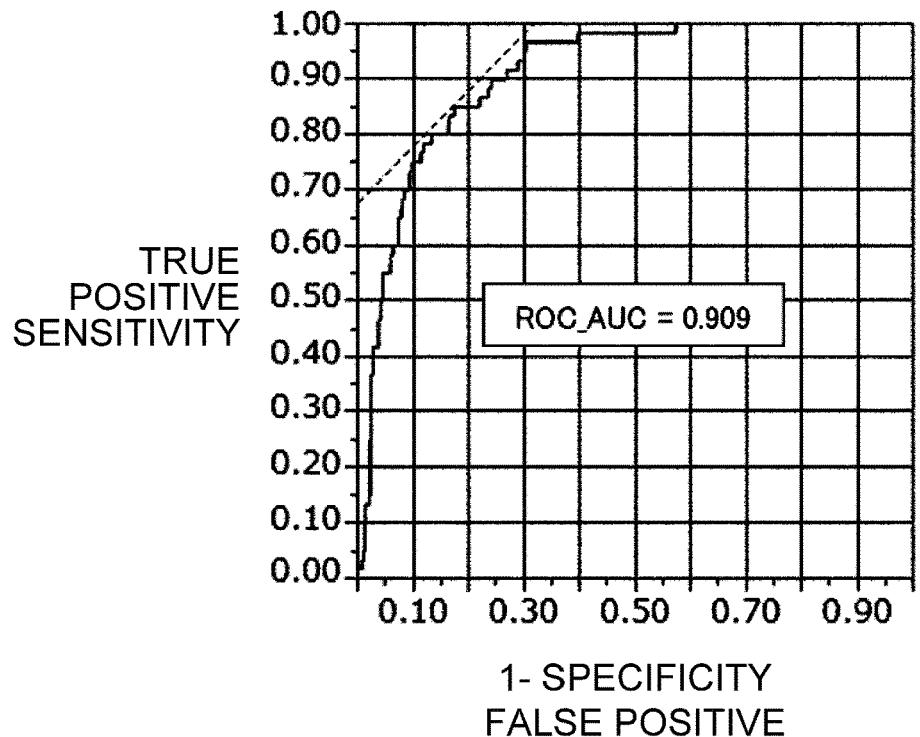
FIG. 6 is a graph illustrating an example of a prediction result in the embodiment of the present invention.

Further, prediction performance was confirmed by an external verification method using test data. Specifically, the program was executed, SDF files of test data were input, and captured images of each compound were generated. The captured images of each compound were input to the learned AlexNet, a median value of output values was obtained, and ROC analysis was performed. The result is illustrated in FIG. 6. As illustrated in FIG. 6, an area (AUC) under a ROC curve was 0.909, which was a high value of 0.9 or more. Note that, a data set used herein was the same as that used in "Tox21 data challenge 2014" held by NIH in 2014, and the AUC value was equivalent to that of top 10 in the competition, although the AlexNet was not adjusted.

Example 2

Figure 7:
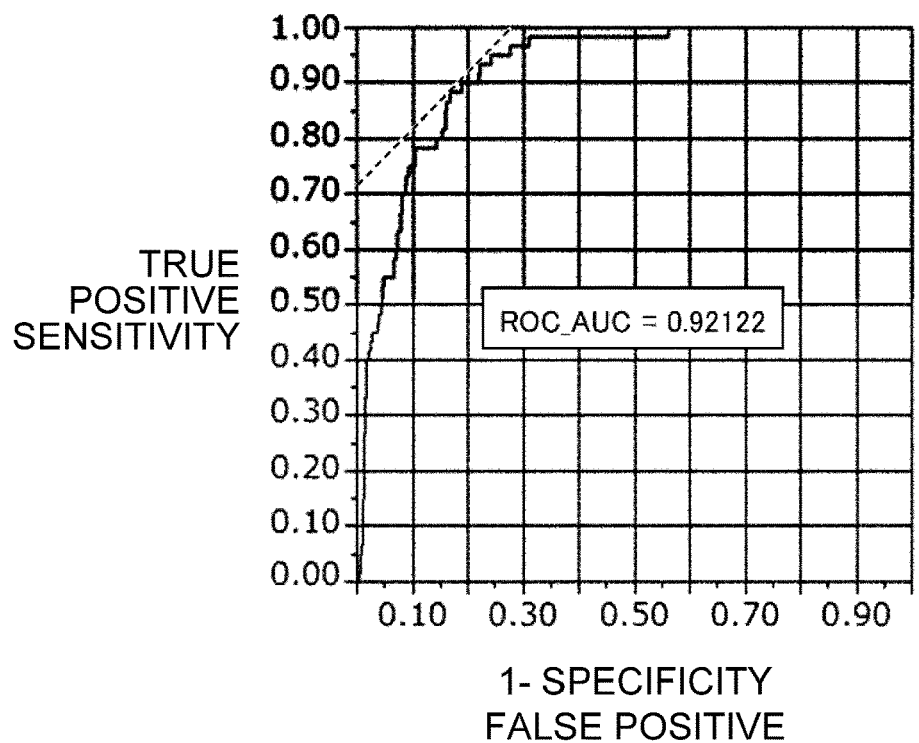
FIG. 7 is a graph illustrating an example of a prediction result in the embodiment of the present invention.

One aspect of the present invention was performed in the same manner as in Example 1 except that Digits was set to have a learning rate=0.0001 and an epoch=8. As a result, as illustrated in FIG. 7, the ROC_AUC value was 0.92122 higher than 0.909 in Example 1. The AUC value was within the values of the top 10 in "Tox21 data challenge 2014", although the AlexNet was not adjusted.

Example 3

One aspect of the present invention was performed using steric structures (SDF file formats) of a total of 4337 compounds and AMES test results (positive or negative) of the respective compounds which were obtained from the appendix of the literature (Derivation and Verification of Toxicophores for Mutagenicity Prediction., J. Med. Chem., 2005, 48, 312-320.). A desired activity to be predicted was mutagenicity (AMES test result). In detail, the test was performed according to the following procedure.

First, the total of 4337 compounds were divided into a learning compound group (4137 compounds) of a prediction model and a compound group (200 compounds) for external verification of prediction results. Then, using Jmol (jmol.sourceforge.net/), structural models of compounds were generated based on SDF files of the learning compound group. A program (learning model input data generating program) for generating 512 captured images (snapshot, size: 512×512, 24 bpp) by capturing images of the respective structural models with rotating the structural models around each of an X-axis, a Y-axis, and a Z-axis in 45-degree increments was executed to generate captured images of each compound. The captured images of each compound were stored in predetermined folders depending on whether the AMES test result of each compound was positive or negative, and an unmodified AlexNet (University of Toronto) was allowed to be learned using Digits (NVIDIA Corp.). In the learning, Digits was set to have a learning rate=0.001 and an epoch=10.

Figure 8:
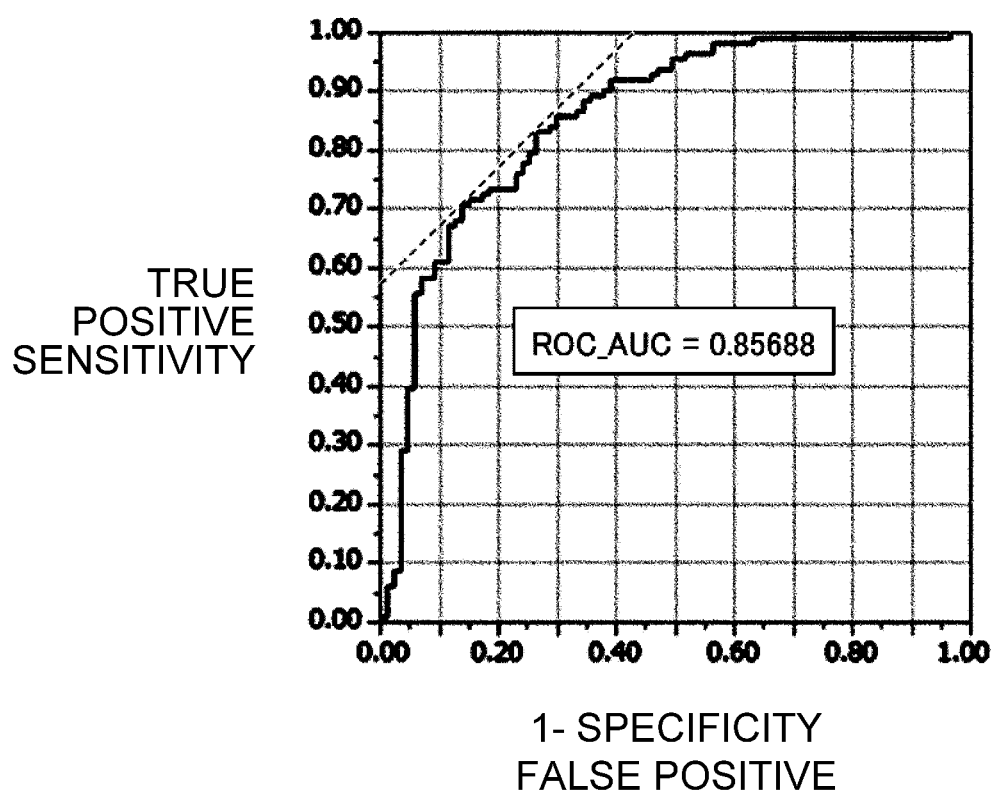
FIG. 8 is a graph illustrating an example of a prediction result in the embodiment of the present invention.

Subsequently, prediction performance was confirmed by an external verification method. Specifically, the program was executed, SDF files of the compound group for external verification were input, and captured images of each compound were generated. The captured images of each compound were input to the learned AlexNet, an average value of prediction results of the positive probability for 512 images per molecule was calculated. That is, the average positive probability for each compound was calculated for 200 molecules. Then, ROC analysis was performed using the experimental result (positive or negative) of the AMES test acquired from the above-described literature and the calculated average positive probability for each compound. The result is illustrated in FIG. 8. As illustrated in FIG. 8, an area (AUC) under a ROC curve was 0.857.

The ROC-AUC value (0.857) obtained by the present Example indicates that the present invention has good versatility compared to a QSAR identification model by a currently-used general machine learning with descriptors. For example, in recent theses which evaluate prediction results by QSAR analysis of the AMES test with the ROC-AUC value, it has been reported that the best value of the ROC-AUC is 0.86 (Benchmark Data Set for in Silico Prediction of Ames Mutagenicity, J. Chem. Inf. Model., 2009, 49 (9), pp 2077-2081, In silico Prediction of Chemical Ames Mutagenicity, J. Chem. Inf. Model., 2012, 52 (11), pp 2840-2847). In the theses, verification has been performed with 5-fold cross verification. In consideration of the fact that the 5-fold cross verification has a higher probability to cause over-learning compared to the external verification and gives better results than the external verification, the AUC value obtained in Example 3 is comparable to the best value in the theses described above.

The present invention can be used to predict toxicity, activity and the like of a compound.

REFERENCE SIGNS LIST 10, 20: structural model
21: atom
22: bond
23: hydrogen atom
100: predicting device (learning model input data generating device)
121: generating unit
122: learning unit
123: predicting unit
124: learning model

What is claimed is:
1. A predicting device which predicts an activity of a target compound based on a structure of the target compound, the predicting device comprising:
    a processor configured to:
    capture images of a three dimensional structural model of the target compound relatively from a plurality of directions with a virtual camera to generate a plurality of captured images as a set of RGB three-color dots with position information in a two-dimensional plane; and predict the activity of the target compound from the plurality of captured images that are generated, using a learning model, the learning model being a neural network, wherein the processor is further configured to learn the learning model and the learning model receives the plurality of captured images as an input.

2. The predicting device according to claim 1, wherein the processor is configured to capture images of the structural model while rotating the virtual camera relatively to the structural model around at least one axis.

3. The predicting device according to claim 1, wherein, in the structural model, a color of an atom of the target compound varies depending on a type of the atom.

4. The predicting device according to claim 1, wherein predicting the activity of the target compound includes predicting at least one of a drug effect, a toxicity, and an enzyme inhibitory activity.

5. The predicting device according to claim 1, wherein each of the plurality of captured images includes at least one of a Ball-and-Stick display in which atoms are indicated by balls and bonds are indicated by sticks, a Wireframe display that shows structural model only by bonds, a Spacefill display that fills a space with atoms, a Surface display that displays a surface of molecules in contact with an aqueous solution, and a Ribbons display that schematically shows a structure of protein.

6. A predicting method of predicting an activity of a target compound, based on a structure of the target compound, the predicting method comprising:

a generating step, by a computer, of capturing images of a three dimensional structural model of the target compound relatively from a plurality of directions with a virtual camera to generate a plurality of captured images as a set of RGB three-color dots with position information in a two-dimensional plane; and a predicting step, by a computer, of predicting the activity of the target compound from the plurality of captured images generated in the generating step, using a learning model, the learning model being a neural network, wherein the learning model receives the plurality of captured images as an input.

7. A non-transitory tangible recording medium which records a predicting program for causing a processor to perform a method comprising:

capturing images of a three dimensional structural model of a target compound relatively from a plurality of directions with a virtual camera to generate a plurality of captured images as a set of RGB three-color dots with position information in a two-dimensional plane; and predicting an activity of the target compound from the plurality of captured images that are generated, using a learning model, the learning model being a neural network, wherein the method further comprises learning the learning model and wherein the learning model receives the plurality of captured images as an input.

8. A learning model input data generating device which generates input data of a learning model, comprising:

the learning model, the learning model being a neural network; and a processor, wherein the learning model is configured to receive, as an input, a plurality of captured images, as a set of RGB three-color dots with position information in a two-dimensional plane, obtained by capturing images of a three dimensional structural model of a target compound with a virtual camera relatively from a plurality of directions, and output prediction information of an activity of the target compound, and wherein the processor is configured to capture the images of the three dimensional structural model of the target compound relatively from the plurality of directions with the virtual camera to generate the plurality of captured images and input the captured images into the learning model.

9. A non-transitory tangible recording medium which records a learning model input data generating program for causing a processor to perform a method comprising:

capturing images, as a set of RGB three-color dots with position information in a two-dimensional plane, of a three dimensional structural model of a target compound relatively from a plurality of directions with a virtual camera to generate a plurality of captured images;

inputting the captured images into a learning model, the learning model being a neural network; and outputting, by the learning model, output prediction information of an activity of the target compound.

* * * * *